United States Patent
Imran

(10) Patent No.: US 11,565,095 B2
(45) Date of Patent: Jan. 31, 2023

(54) DEVICES, SYSTEMS, AND METHODS FOR DELIVERING THERAPEUTIC AGENTS INTO A STOMACH WALL

(71) Applicant: Rani Therapeutics, LLC, San Jose, CA (US)

(72) Inventor: Mir Imran, Los Altos Hills, CA (US)

(73) Assignee: Rani Therapeutics, LLC, San Jose, CA (US)

( * ) Notice: Subject to any disclaimer, the term of this patent is extended or adjusted under 35 U.S.C. 154(b) by 198 days.

(21) Appl. No.: 16/805,317

(22) Filed: Feb. 28, 2020

(65) Prior Publication Data

US 2020/0276425 A1 Sep. 3, 2020

Related U.S. Application Data

(60) Provisional application No. 62/821,250, filed on Mar. 20, 2019, provisional application No. 62/812,867, filed on Mar. 1, 2019.

(51) Int. Cl.
*A61M 31/00* (2006.01)
*A61M 5/142* (2006.01)
(Continued)

(52) U.S. Cl.
CPC ...... *A61M 31/002* (2013.01); *A61M 5/14276* (2013.01); *A61M 25/0116* (2013.01);
(Continued)

(58) Field of Classification Search
CPC . A61M 5/14276; A61M 31/002; A61M 31/00
See application file for complete search history.

(56) References Cited

U.S. PATENT DOCUMENTS 8,562,589 B2 10/2013 Imran
8,734,429 B2 5/2014 Imran et al.
(Continued)

FOREIGN PATENT DOCUMENTS

EP 2 238 885 A1 10/2010
WO WO-2018213582 A1 11/2018

OTHER PUBLICATIONS

International search report with written opinion dated May 15, 2020 for PCT/US2020/020540.
(Continued)

*Primary Examiner* — Jenna Zhang
(74) *Attorney, Agent, or Firm* — Foley & Lardner LLP

(57) ABSTRACT

Embodiments of the invention provide swallowable devices, preparations and methods for delivering drugs and other therapeutic agents (TA) within the GI tract and in particular to an antrum wall (AW). Particular embodiments provide a swallowable device (SD) such as a capsule for delivering drugs or other TA into the AW. The SD may contain a pressure sensitive component or assembly which triggers release and insertion of a therapeutic agent preparation (TAP) comprising at least one TA into the AW in response to external pressure, such as pressure applied to the swallowable capsule or other SD by antrum contractions. Particular embodiments of the SD may be shaped so that they self-align within an antrum to properly orient before injection of the TAP into the AW. Embodiments of the invention are particularly useful for orally delivering drugs or other TAs which are degraded within the GI tract and require parenteral injection.

23 Claims, 7 Drawing Sheets

(51) Int. Cl.
*A61M 25/10* (2013.01)
*A61M 25/01* (2006.01)

(52) U.S. Cl.
CPC ............ *A61M 25/10* (2013.01); *A61M 31/00* (2013.01); *A61M 31/007* (2013.01); *A61M 2205/3331* (2013.01); *A61M 2205/3344* (2013.01); *A61M 2205/3368* (2013.01); *A61M 2205/8231* (2013.01); *A61M 2210/1042* (2013.01); *A61M 2210/1053* (2013.01); *A61M 2230/208* (2013.01); *A61M 2230/60* (2013.01)

(56) References Cited

U.S. PATENT DOCUMENTS

| | | | |
|---|---|---|---|
| 8,764,733 | B2 | 7/2014 | Imran |
| 8,809,269 | B2 | 8/2014 | Imran |
| 8,809,271 | B2 | 8/2014 | Imran |
| 8,846,040 | B2 | 9/2014 | Imran |
| 8,969,293 | B2 | 3/2015 | Imran |
| 8,980,822 | B2 | 3/2015 | Imran |
| 9,149,617 | B2 | 10/2015 | Imran |
| 9,259,386 | B2 | 2/2016 | Imran |
| 9,283,179 | B2 | 3/2016 | Imran |
| 9,284,367 | B2 | 3/2016 | Imran |
| 9,402,806 | B2 | 8/2016 | Imran |
| 9,402,807 | B2 | 8/2016 | Imran |
| 9,415,004 | B2 | 8/2016 | Imran |
| 9,629,799 | B2 | 4/2017 | Imran |
| 9,757,548 | B2 | 9/2017 | Imran |
| 9,861,683 | B2 | 1/2018 | Imran |
| 10,098,931 | B2 | 10/2018 | Morales et al. |
| 10,220,003 | B2 | 3/2019 | Imran et al. |
| 10,227,403 | B2 | 3/2019 | Imran et al. |
| 10,300,259 | B2 | 5/2019 | Ziaie et al. |
| 10,603,275 | B2 | 3/2020 | Imran et al. |
| 2004/0253304 | A1 | 12/2004 | Gross et al. |
| 2007/0010709 | A1 | 1/2007 | Reinschke |
| 2007/0250132 | A1* | 10/2007 | Burnett ................. A61F 5/0036 607/40 |
| 2010/0286628 | A1* | 11/2010 | Gross .................... A61M 25/04 604/285 |
| 2011/0160699 | A1* | 6/2011 | Imran ................ A61K 38/2235 604/93.01 |
| 2011/0208270 | A1 | 8/2011 | Imran et al. |
| 2015/0064241 | A1 | 3/2015 | Conrad |
| 2016/0235663 | A1 | 8/2016 | Zou et al. |
| 2016/0256106 | A1* | 9/2016 | Krasnow ............ A61B 5/15125 |
| 2017/0066824 | A1 | 3/2017 | Imran et al. |
| 2017/0066841 | A1 | 3/2017 | Imran et al. |
| 2017/0265598 | A1 | 9/2017 | Beers et al. |
| 2020/0276426 | A1 | 9/2020 | Imran |

OTHER PUBLICATIONS

Laulicht, et al. Understanding Gastric Forces Calculated From High-Resolution Pill Tracking. Proc Natl Acad Sci USA. May 4, 2010;107(18):8201-8206. doi: 10.1073/pnas.1002292107. Epub Apr. 19, 2010.

Fiume et al., "Safety Assessment of Nitrocellulose and Collodion as Used in Cosmetics," International Journal of Toxicology, vol. 35 (Supplement I) 50S-59S (Jul. 2016).

International Search Report with Written Opinion dated Jun. 11, 2020 for PCT/US2020/020544.

Pi et al., "A Novel Micro-Fabricated Thruster for Drug Release in Remote Controlled Capsule," Sensors and Actuators A: Physical, vol. 159, pp. 227-232 (Mar. 2010).

Steiger et al., "Ingestible Electronics for Diagnostics and Therapy," Nature Reviews Materials, vol. 4, pp. 83-98 (Feb. 2019).

Yu et al., "A Smart Capsule with GI-Tract-Location-Specific Playload Release," IEEE Transactions on Biomedical Engineering, vol. 62, No. 9, pp. 2289-2295 (Sep. 2015).

* cited by examiner

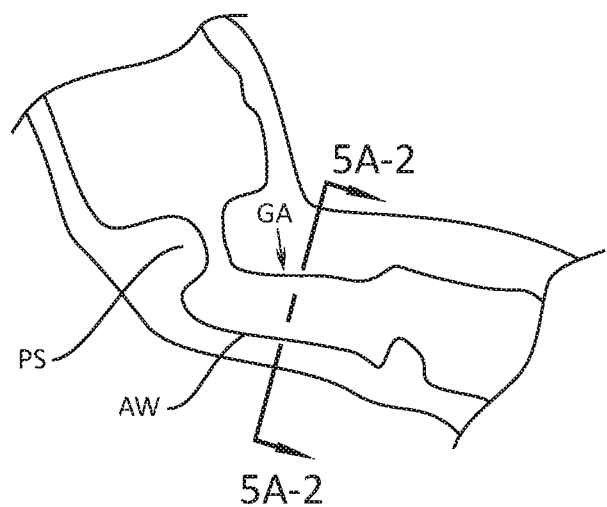 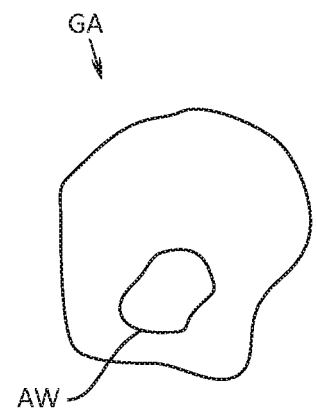
FIG. 5A-1          FIG. 5A-2
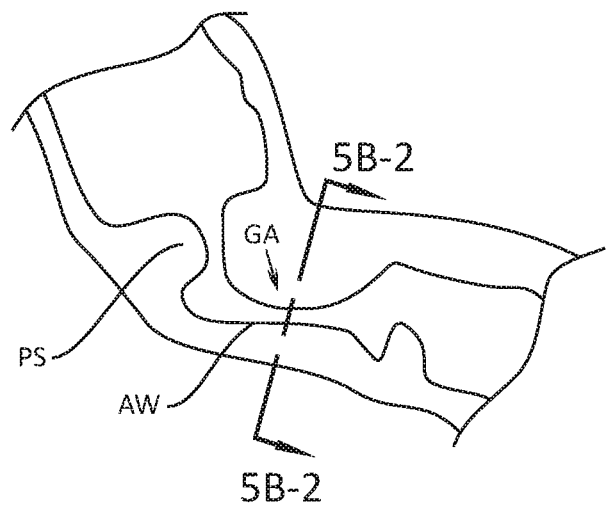 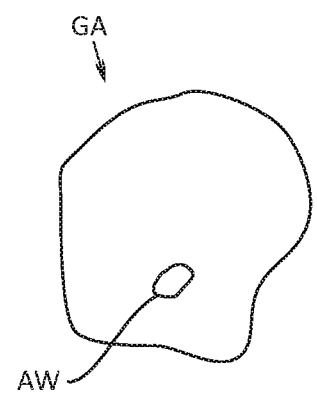
FIG. 5B-1          FIG. 5B-2

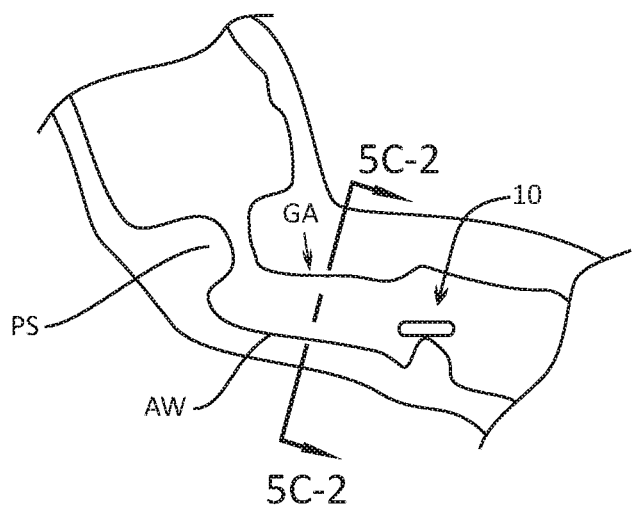 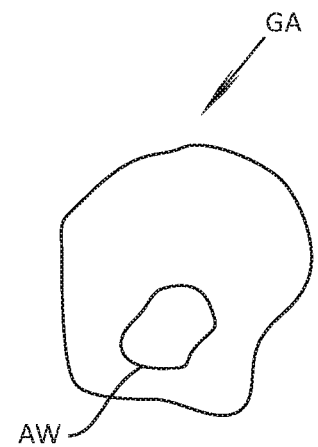
FIG. 5C-1  FIG. 5C-2
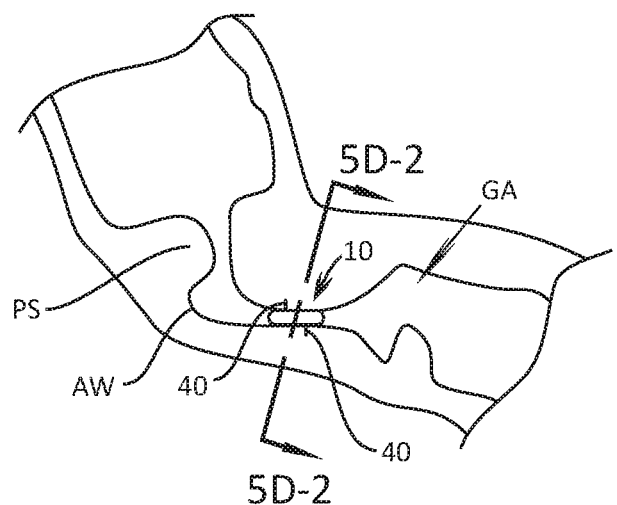 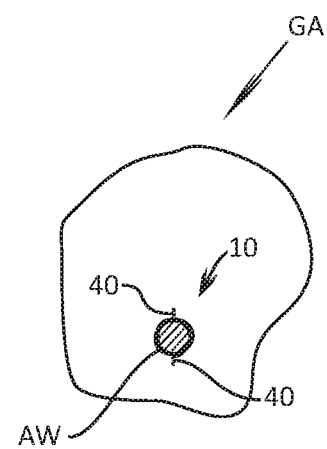
FIG. 5D-1  FIG. 5D-2

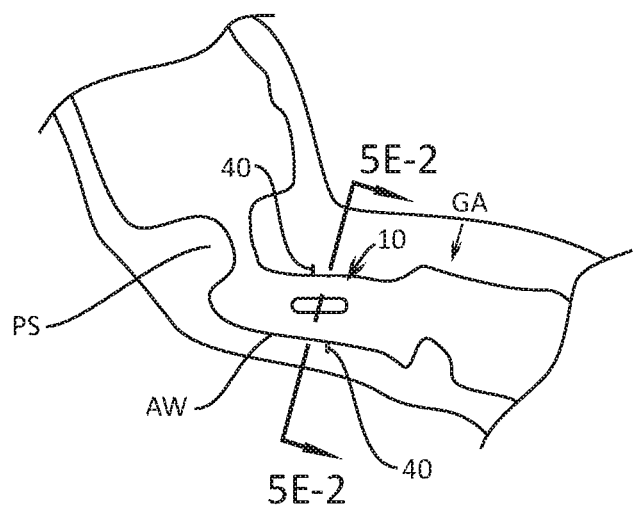 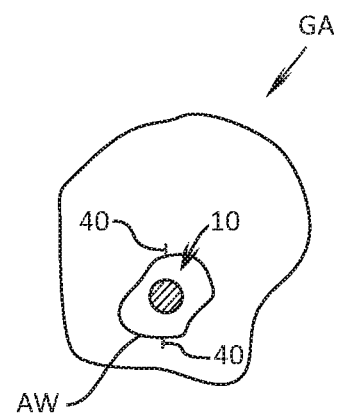
FIG. 5E-1　　　　　FIG. 5E-2
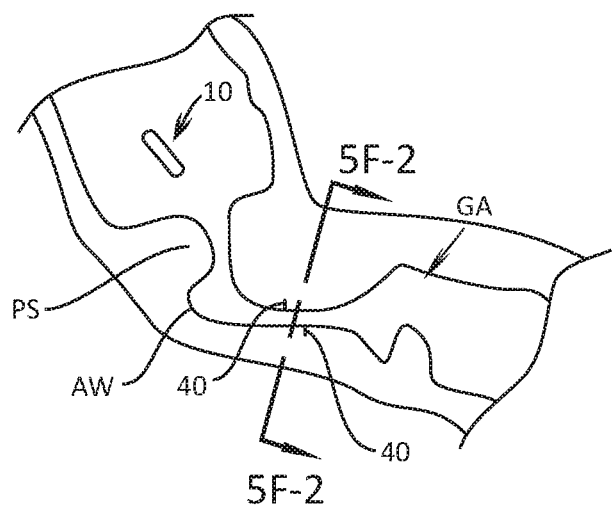 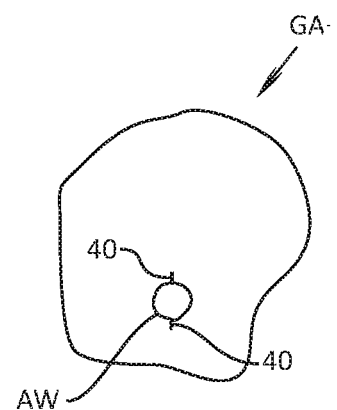
FIG. 5F-1　　　　　FIG. 5F-2

DEVICES, SYSTEMS, AND METHODS FOR DELIVERING THERAPEUTIC AGENTS INTO A STOMACH WALL

CROSS-REFERENCES TO RELATED APPLICATION

This application claims priority to, and the benefit of, U.S. Provisional Patent Application Ser. Nos. 62/812,867, filed on Mar. 1, 2019, and 62/821,250, filed on Mar. 20, 2019, the full disclosure of both of which is incorporated by reference herein for all purposes.

BACKGROUND

Technical Field

Embodiments of the invention relate to swallowable drug delivery devices. More specifically, the present invention relates to swallowable drug delivery devices for delivering therapeutic agents into the gastric antrum or other portion of the stomach wall.

While there has been an increasing development of new drugs in recent years for the treatment of a variety of diseases, many including proteins, antibodies, peptides, and other labile medicaments have limited use because they cannot be given orally and thus typically require intravenous or other form of parenteral administration (e.g., intramuscular, etc.) to avoid degradation. The inability to deliver the drug orally may arise from any one of a number of reasons including poor oral toleration with complications including gastric irritation and bleeding, breakdown/degradation of the drug compounds in the stomach, and poor, slow or erratic absorption of the drug.

Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery.

Thus, there is a need for additional, alternative, and improved methods, devices, and articles for the oral delivery of drugs and other therapeutic agents. In particular, it would be desirable to provide delivery vehicles and constructions that allow the oral administration of a drug and subsequent injection or other delivery of the drug into a wall of the patient's gastric antrum and other targeted regions of a patient's gastrointestinal (GI) tract.

US2017/0265598 describes an implantable system which injects a drug into a patient's antrum to induce contractions as part of an obesity treatment. Patents and published patent applications having common inventorship and/or common ownership with the present application which describe swallowable capsules for injecting drugs into an intestinal or other wall in the GI tract include U.S. Pat. No. 9,149,617; US2011/0208270; and US20120010590. Published PCT Application WO2018/213582 describes a capsule with a spring-loaded medicament structure for injection drugs into a stomach wall.

BRIEF SUMMARY

Various embodiments of the invention provide devices, systems, articles, formulations, kits and methods for delivering drugs and other therapeutic agents into a wall of a patient's stomach including the gastric antrum or other wall of the patient's GI tract. In many embodiments, the invention provides wallowable capsules and other swallowable devices suitable for the delivery of drugs and other labile therapeutic agents which are poorly absorbed, poorly tolerated, and/or degraded within the gastrointestinal (GI) tract, such as proteins, polypeptides and antibodies. While particularly useful for the injection of such labile therapeutic agents into a wall of the gastric antrum, embodiments the present invention will also find use with other medicaments and introduction into other locations in the GI tract such as the walls of the small, large intestine, buccal surfaces in the mouth and elsewhere in the patient's body.

In many embodiments, the invention provides swallowable drug delivery devices (also described herein as swallowable device) which may include sensors, such as pressure sensors, or other mechanisms or sensing means that can detect when the swallowable device has entered the gastric antrum. Particular embodiments comprise a swallowable device, such as a capsule, for delivering drugs and other therapeutic agents into the wall of the patient's gastric antrum. For example, the device may be a swallowable capsule configured to detect or respond to pressure exerted on an exterior of the device by contractions of the antrum and to inject or otherwise deliver the therapeutic agent while the capsule is in the antrum. Such swallowable capsules and other devices are typically further configured to self-align when in the antrum so that the drug or other therapeutic agent is injected from the capsule in a predetermined direction into an adjacent wall of the gastric antrum. Preferably, the direction is substantially perpendicular to the wall of the antrum or other wall portion of the stomach or GI tract. However, other directions are also considered such as at a 45° angle. In particular embodiments, the direction can be in a range spanning about 45° on either side of the longitudinal axis of the antrum wall.

Specific embodiments of the invention are particularly useful for the delivery of solid dosage forms of drugs and other therapeutic agents particularly those which would otherwise be degraded or otherwise lose their bioactivity from exposure to digestive fluids in the GI tract if not delivered into GI wall tissue. Other embodiments are useful for the delivery of liquid, gel, powder, and other conventional medicament/drug forms particularly those which would otherwise be degraded or otherwise lose their bioactivity from exposure to digestive fluids in the GI tract if not delivered into GI wall tissue. The exemplary solid dosage forms will often be self-penetrating, for example having a sharpened, pointed, tapered, or other shaped distal tip to facilitate penetration through a surface of an antrum (aka antral) or other luminal wall of the GI tract. Such self-penetrating solid dosage forms are sometimes referred to herein as tissue-penetrating members (TPM) hereinafter. Many embodiments of the invention will be capable of achieving a rapid release of a drug into the blood stream via oral delivery with minimum or no degradation resulting from passage through any portion of the GI tract.

In a first specific aspect, an embodiment of the invention comprises a swallowable device for delivering a therapeutic agent preparation into a wall of a patient's GI tract such as the antral wall (also referred to as the antrum wall) of the stomach. The device may comprise a swallowable capsule or other enclosure having a capsule wall, where the therapeutic agent preparation is held inside the capsule or other enclosure. A driver is also contained within the capsule and configured to advance the therapeutic agent through the capsule wall and into the antral wall or other GI wall when a selected condition around the capsule is detected such as proximity of the capsule to antrum wall and/or an amount of pressure or force exerted by the antrum wall onto the capsule wall, particularly an amount of pressure or force indicative of a peristaltic contraction of the antrum wall around the capsule. A sensor on or within the swallowable device senses when the capsule wall is adjacent to the antrum (or other GI) wall such as occurs when the antrum wall contracts around (e.g., squeezes) a portion of the capsule due to a peristaltic contraction. The driver is configured to advance the therapeutic agent through the capsule wall and into the stomach wall when the sensor senses that the capsule wall is adjacent to the antrum wall or other GI wall. In particular embodiments, proximity of the capsule to the antrum wall, for example due to a peristaltic contraction around a portion of the capsule, can be determined by the amount of force applied by the antrum wall to the capsule wall being in a range from about 200 to 3100 dynes with narrower ranges described in more detail herein. In many embodiments, the driver and sensor are configured to response quickly enough (e.g. within a few tenths of a second or less) so as to advance the therapeutic agent into the antrum wall while antrum (or other GI wall) is contracting around (e.g., squeezing) or otherwise in contact with at least a portion of the capsule wall.

In specific aspects and embodiments, the swallowable capsule wall can comprise a cylindrical shell, where the capsule may be degradable in all or portions of the patient's GI tract or may be non-degradable in all or portions of the patient's gastrointestinal tract. For example, the capsule wall may be fabricated fin whole or in part from a material which degrades in specific regions of the GI tract, for example comprising an enteric material which degrades at a pH equal to or greater than about 6.5, but which remains intact in the stomach in particular the antrum where the drugs other therapeutic agent disposed or carried by the capsule will typically be released in exemplary embodiments herein.

Exemplary drivers according to the embodiments of invention may comprise mechanical, chemical, or other components capable of selectively delivering the drug other therapeutic agent into the antrum wall (or other wall of the GI tract) in response to a trigger from the sensor. For example, according to one or more embodiments the driver may be a compressed spring, may be a balloon, or may be another mechanical component capable of storing and/or generating energy as needed to advance the therapeutic preparation. Alternatively, in the disclosed embodiments, the driver may comprise a chemical propellant material which can release sufficient energy to drive a mechanical element to advance the therapeutic agent through the capsule wall. In a particular embodiment described in more detail below, the driver comprises a nitrocellulose or other chemical propellant which may be ignited by an electrical or other ignition or initiation source.

In various embodiments, the swallowable devices of the present invention may include two or more drivers configured to drive therapeutic agent(s) in at least two directions, optionally including three drivers, four drivers, or more, which may direct the therapeutic agent(s) in three, four, or more directions. The at least two drivers may be further be configured to drive the therapeutic agents in at least two diametrically opposed directions. Similarly, when three or more drivers are utilized, the drivers may direct the therapeutic agent(s) in symmetric or asymmetric patterns.

Suitable sensors according to embodiments of invention may comprise an electronic sensor which generates a signal representative of proximity, such as external pressure on a wall or other external region of the swallowable capsule. The electronic sensor may comprise a solid state pressure transducer, e.g. a piezoelectric transducer, or other transducer which can be miniaturized to fit in or through the capsule wall. Other sensors which can employed to detect proximity include on or more of capacitance, resistance (electrical) or optical based sensors.

When employing an electronic sensor, such as a piezoelectric or other pressure/force transducer, the swallowable devices will typically further comprise a controller or other electronic circuit (analogue or digital) which receives the pressure/force or other sensor signal from the sensor and generates a trigger signal when the swallowable capsule is adjacent the antrum (or other section of the GI wall). The state of adjacency can be determined, for example, when a pressure sensor detects a pressure which exceeds a predetermined threshold value. Such threshold values of applied force encountered when the swallowable capsule is in a patient's antrum will typically be in the range from about 200 to 3100 dynes usually in the range from 200 to 750 dynes, and often in the range from about 400 to 750 dynes of applied force. For the broadest range of forces, this may correspond to about 300 to 1100 dynes/cm$^2$ of pressure. Specific allowances can be made for such threshold forces when the capsule is taken in the fed vs a fasted state. In the fed state, the triggering threshold can be in the range of about 570 to 750 dynes of applied force (corresponding to about 835 to 1086 dynes/cm$^2$ of pressure), corresponding to while in the fasted state the triggering threshold can be in the range of about 200 to 610 dynes of applied force (corresponding to about 300 to 900 dynes/cm$^2$ of pressure). One or more of the aforementioned forces may be converted to pressures using equations and computational methods known in the medical sensor arts. Further description of forces and pressures in the GI tract may be found in the paper by Laulichta et al. entitled "Understanding gastric forces calculated from high-resolution pill tracking" PNAS, May 4, 2010, vol. 107, no. 18. pages 8201-8206 which is fully incorporated by reference herein for all purposes.

In other embodiments, the pressure or other proximity sensor may comprise a mechanical fluidic element which changes state in response to changes in proximity or external pressure on a wall or other external region of the swallowable capsule. In such instances, the trigger will comprise a mechanical or fluidic trigger element which responds to a change of state of the mechanical or fluidic sensor and mechanically releases the driver to advance the therapeutic agent through the capsule wall and into the antrum or other GI wall. In preferred embodiments, the trigger and driver are configured to sense and respond to quickly enough to advance the therapeutic agent through the capsule wall and into the antrum wall while the capsule wall is still in proximity to the antrum wall (or other wall of the GI tract). Such mechanical or fluidic sensor elements will typically be configured to respond to the same pressure/force ranges set forth above which are typical of the antrum. However, other forces are also contemplated.

In many instances, the therapeutic agent being delivered by the swallowable device will comprise a solid dosage form having a tissue-penetrating end that is advanced into the intestinal wall by the driver. Such solid dosage forms often comprise an active agent compressed or otherwise formed with at least one of an excipient or a binder into an elongate member having a tapered, sharpened, or honed tip at one end thereof which may be straight or curved. However other shapes are also contemplated. In other instances, the therapeutic agent may comprise a liquid dosage or other non-solid form which is advanced into the intestinal wall through a hollow needle or other injector by the driver or related device. Also, in one or more instances, the therapeutic agent may comprise a biological molecule or biological substance (e.g., cells) which would otherwise be chemically degraded by digestive fluids in the GI tract (e.g. small intestine fluids) if not delivered into the antrum or other luminal wall of the GI tract. Such biological molecules may include various biologics which include one or more of proteins, antibodies, polypeptides and other molecules which are produced by cells or other biological process.

In a second aspect, embodiments of the invention provide a method for delivering a therapeutic agent into an antral wall of a patient's intestinal tract comprises providing a swallowable capsule having the therapeutic agent preparation held inside. The patient ingests the swallowable capsule, and the capsule passes through the patient's stomach and into the patient's gastric antrum. While in the stomach, the therapeutic agent remains inside of the swallowable capsule, and upon entering the antrum, the capsule senses pressure applied externally to an exterior surface of the capsule by contractions of the antrum. The capsule is configured such that it will inject the therapeutic agent into the antral wall when the sensed pressure exceeds a predetermined threshold value and/or frequency of contractions. In particular embodiments, the capsule is configured to sense peristaltic contraction having a particular applied force/pressure and contraction frequency.

The predetermined threshold value will typically be selected based on a peak pressure applied by the antral wall, though other pressures and physiologic events are also considered. The peak pressure may be an average value for a population or in other instances may be determined for a particular patient. In either case, the threshold value selected to trigger release of the therapeutic agent will typically be in a range from about 50% to 95% of the peak pressure expected to be applied by the antral wall, often being from 60% to 90% at the peak pressure, will often being from 75% to 85% of the peak pressure, and often being about 80% of the peak pressure. As described above, in addition to sensed peak pressure the triggering threshold or event may also incorporate a frequency of contractions. In one or more embodiments the triggering frequency of contractions may correspond to a range from 3 to 6 contractions per second, more preferably 3 to 4 and still more preferably about 3 contractions per second which corresponds to a contractile motion of the antrum where the antrum tightly contracts around in food in a grinding motions which is part of the antrum pump function described herein. In particular implementations, the capsule would remain in the antrum in an un-deployed state until a requisite number of contractions have been sensed to determine a frequency of contractions (e.g., by a processor other logic means) at which point the capsule would eject the therapeutic agent into the antrum wall. In related implementations, the capsule remains in the antrum until the requisite number of contractions are sensed which have a peak or a % of a peak pressure (e.g., 50 to 95%, et) described herein. According to some embodiments, the patient may first swallow a test capsule or capsule mimic which does not necessarily contain a trigger and therapeutic agent, but rather whose main function is to record the applied pressure to the capsule through a number of antral peristaltic contractions and then calculate and transmit to an external device various information related to those contractions including one or more of average peak peristaltic pressure, frequency and period of contraction. That information can then be downloaded from the external device to processor or other control module incorporated into the capsule and then utilized to trigger or otherwise control the release of therapeutic agent into antral wall.

The swallowable capsule will usually be configured so that it will self-align when present in the antrum particularly when the antrum undergoes contractions such as from peristaltic contractions. For example, the capsule may be elongated, such as being cylindrical with rounded distal and proximal ends and have an axis which aligns with a luminal direction of the patient's gastric antrum as the capsule passes from the stomach into the gastric antrum. By orienting the capsule in this manner, the therapeutic agent may be injected in a lateral or other preselected direction (e.g., at an acute angle such as 45°) relative to a longitudinal axis of the capsule so that there will be higher assurance of the therapeutic agent entering a given location on the antral wall.

The force/pressure from the antrum wall contracting around the capsule may be sensed in various ways. For example, according to one embodiment, the swallowable capsule may comprise an electronic pressure transducer, such as a solid state piezoelectric transducer, incorporated into a wall of the swallowable capsule. In such instances, the electronic transducer may be coupled to a device or other means for triggering a propellant to advance the therapeutic agent into the antral wall when the sensed pressure exceeds the predetermined threshold value. In some embodiments, the electronic transducer may be directly or otherwise operably coupled to the propellant so as to trigger the propellant to advance the therapeutic agent into the antral wall.

In other instances, the pressure may be sensed by a mechanical or fluidic pressure transducer incorporated into the swallowable capsule for example, into the capsule wall. Such mechanical or fluidic transducer may be coupled to device or other means to trigger a balloon, a compressed spring, or other such mechanical element to advance the therapeutic agent into the antral wall when the sensed pressure exceeds the predetermined value. In some embodiments, the mechanical or fluidic pressure transducer may be directly or otherwise operably coupled to the balloon, compressed spring, or other such mechanical element so as to trigger balloon, compressed spring, or other such mechanical element advance the therapeutic agent into the antral wall.

In still other instances, the therapeutic agent may be injected in at least two different directions from the capsule. For example, the therapeutic agent may be injected in two diametrically opposed directions from the capsule such that the forces acting against the capsule as the agents are injected balance one another. In use, in additional to delivering increased amounts of drug such embodiments provide for improved reliability of drug into the antral wall (or other location in the GI tract) by offsetting any forces (e.g., recoil forces) tending to push the capsule away from the antral surface when the solid drug dosage is ejected from the capsule by the driver such as a nitrocellulose or other ignitable chemical propellant.

In all such methods, the therapeutic agent may be in a variety of forms including for example, solid dosage form, a liquid dosage form or other form, such as powder, gel, or the like as wells combinations of any of aforementioned forms. In preferred instances, the therapeutic agent will be in a solid dosage form having a self-penetrating distal tip to enhance advancement into the antral wall or other wall portion of the GI tract. However, other embodiments contemplate forms of a solid therapeutic agent without the self-penetrating distal tip. For solid dosage forms of the therapeutic agent, the dimensions and shape of the solid dosage may be adjusted to the particular target delivery area in the GI tract e.g., the antrum wall.

In yet another aspect of the invention, a swallowable device for delivering a therapeutic agent preparation into a wall of a patient's stomach (such as the antral wall) or other portion of the GI tact comprises a capsule, a therapeutic preparation, a sensor, and an ejection means. The capsule is sized to pass through the patient's gastro-intestinal tract and has a wall including opposed side portions and opposed end portions. The capsule preferably has an elongated shape configured to longitudinally orient within the antrum of the stomach during a peristaltic contraction of the stomach such that a side portion of the capsule wall is adjacent wall of the antrum. The capsule carries a therapeutic preparation, typically comprising a therapeutic agent which is shaped as a tissue-penetrating member (TPM). A sensor is disposed in a side wall portion of the capsule wall, the sensor being configured to sense a force/pressure applied by the antral wall to the capsule wall (or other exterior region of the capsule) as a result of peristaltic contraction of the antrum and generate an output corresponding to otherwise containing information on the sensed pressure/force. An ejection means is operably coupled to the sensor and the tissue penetrating member. When the sensor senses a selected amount of force/pressure applied to the capsule wall (other capsule exterior region) from the antrum wall (or other GI wall portion), it generates an output, which results in the ejection means ejecting the tissue-penetrating member through the capsule wall and into the antrum wall (or other wall of the GI tract or surrounding tissue) desirably, while the capsule wall is still in proximity to the antrum wall (or other wall of the GI tract). In this way, the ejector means can eject the tissue-penetrating member from the capsule into antral wall tissue in response to output of the sensor. The amount of pressure/force to trigger the ejection means is desirably selected to improve or enhance the delivery of the tissue penetrating member into the antrum wall (or other GI wall), e.g., by assuring that antrum wall is in close proximity and/or is squeezing the capsule with sufficient force such that the tissue penetrating member into the antrum wall (or other GI wall).

The ejection means may comprise any energy storage mechanism, such as a spring, a compressed air spring, a chemical reservoir, or the like. In specific embodiments, the ejection means comprises a chemical, such as a combustible propellant or other reactants that may be ignited to release energy to drive the tissue-penetrating member into tissue. For example, the ejection means may comprise one or more of chemical reactants, chemical reactant impregnated fibers, chemical reactant impregnated membranes, nitrate-impregnated fibers or membranes, nitrocellulose, or the like.

In various embodiments, the pressure sensor may be an electronic pressure sensor, a mechanical pressure sensor, or combinations thereof. In exemplary embodiments, the pressure sensor comprises a solid state, piezoelectric sensor calibrated to detect pressures in the ranges set forth above. Also, according to some embodiments, the patient may first take a test or measurement capsule which is solely configured to measure applied pressure/force to the capsule wall from antrum contraction (e.g., it does not contain a therapeutic agent, driver, ejection means etc.) and then transmit that data to external device. In particular embodiments the pressure sensor and or other proximity sensor may positioned in close proximity (e.g., about 1 to 5 mm) to where the solid drug dosage (e.g., in the form of a tissue penetrating member) exits the capsule so that there can be increased assurance that the antrum wall is indeed in contact with the capsule surface when the driver is triggered to eject that solid drug dosage into the antrum wall. In this way, there is increased reliability that the solid drug dosage is delivered into the antral wall or other desired location in the GI Tract. In still other embodiments, the ejection means may comprise a bellows (or like structure) for example, having opposed surfaces for advancing a pair of tissue-penetrating members in opposed directions.

In yet another embodiment, a swallowable for delivering a therapeutic agent preparation into a wall of the patient's stomach comprises a capsule, a therapeutic preparation, a sensor, a logic means, and an ejection means. The capsule, the therapeutic preparation, the sensor, and the ejection means may be as just described. The logic means is configured to analyze electrical outputs from the pressure sensor and generate a trigger signal when a peristaltic condition in the antrum (or other portion of the stomach or GI tract) is detected. According to various embodiments, the logic means may correspond to a microprocessor or other digital processor or an analog device.

In some embodiments, the TPM contains the drug or other therapeutic agent and is configured to be inserted into the antral or other intestinal wall by expansion of a driving member, such as a propulsive element, a delivery balloon, or other expandable delivery means. The TPM typically, comprises a shaft including a proximal portion detachably coupled to the delivery device, a tissue penetrating distal portion, and optionally a retaining feature for retaining the tissue penetrating member within the antral or other region of the intestinal wall. The tissue penetrating end will typically be tapered, chamfered, or otherwise formed or sharpened to enhance tissue penetration when driven into tissue. The tissue retention feature may be a hook, barb, bifurcation, or the like which allows advancement into the tissue but resists retraction from the tissue. In various embodiments, the TPM need not include a retaining feature, but instead can have a shape or otherwise be configured to be retained in the stomach or intestinal wall without the retaining feature.

The TPM will typically be formed at least in part from a therapeutic agent preparation including a drug or other therapeutic agent that is configured to dissolve or otherwise be absorbed within the intestinal wall so as to deliver the therapeutic agent preparation to the patient's blood stream. The therapeutic agent preparation may also include one or more pharmaceutical excipients known in the art, e.g., disintegrants, binders etc. The TPM is desirably configured to penetrate a selected distance into the stomach, intestinal wall or surrounding tissue of either so as to deliver therapeutic agent to a particular tissue layer of the intestinal wall, for example the mucosal layer, submucosal layer, etc. This can be achieved through the use of stops positioned on the TPM shaft and/or configuring the TPM shaft to bend or even shear once it penetrates a selected distance in the intestinal wall.

Typically, the drug or other therapeutic agent delivered by the TPM will be mixed in with a biodegradable polymer such as PEO (polyethylene oxide), PGLA and/or a sugar such as maltose. In such embodiments, the TPM may comprise a substantially heterogeneous mixture of drug and biodegradable polymer. Alternatively, the penetrating member may include a portion formed substantially from biodegradable polymer and a separate section or compartment that is formed from or contains the drug or other therapeutic agent. For example, in one embodiment, the TPM may comprise an outer shell of biodegradable material with a hollow core which is fitted with a slug (e.g., cylinder shaped)

of the therapeutic agent. The tip or tissue penetrating portion of the TPM can include a harder material such as a sugar or a metal (e.g., magnesium) so as to be able to readily penetrate tissue including for example tissue in the antrum wall or other wall of the intestinal tract (e.g., the wall of the small intestine). Once placed in the stomach wall (e.g., the antrum wall) or other wall of the GI tract, the tissue penetrating member is degraded by the interstitial fluids within the wall tissue, the drug dissolves in those fluids and is absorbed into the blood stream by the capillaries in or around the stomach, intestinal or other GI wall tissue (e.g., the peritoneum). The TPM may also include one or more tissue retaining features such as a barb or hook to retain the penetrating member within the tissue of the stomach wall or other wall of the GI tract (e.g., an intestinal wall) after advancement. The retaining features can be arranged in various patterns to enhance tissue retention such as two or more barbs symmetrically distributed around the member shaft. However, the TPM can also be retained in the stomach wall or other GI tract wall through other means such as by a reverse taper or other shape. The reverse taper shape may also be combined with one or more retaining features to further enhance retention.

The drug or other therapeutic agent can be in solid form and then formed into the shape of the tissue penetrating member using molding or other like method or may be in solid or liquid form and then added to the biodegradable polymer in liquid form with the mixture then formed into the Tm using molding or other forming method known in the polymer arts. Desirably, embodiments of the tissue penetrating member comprising a drug and degradable polymer are formed (e.g., cured) at temperatures which do not produce any substantial thermal degradation of the drug including drugs such as various peptides and proteins. This can be achieved through the use of room-temperature curing polymers and room temperature molding and solvent evaporation techniques known in the art. In particular embodiments, the amount of thermally degraded drug within the tissue penetrating member is desirably less than about 10% by weight, more preferably less than 5% and still more preferably, less than 1%. The thermal degradation temperatures for a particular drug are known or can be determined using methods known in the art and then this temperature can be used to select and adjust the particular polymer processing methods (e.g., molding, curing. solvent evaporation etc.).

In other aspects, the present invention provides therapeutic agent preparations for delivery into the wall of the small intestine (or other wall of a lumen in the GI tract) using embodiments of the swallowable device described herein. The preparation comprises a therapeutically effective dose of at least one therapeutic agent (e.g., insulin, incretin, an anti-seizure compound, NSAIDs, an antibiotic etc.). The preparation may comprise a solid, liquid, gel and combinations thereof and can include one or more pharmaceutical excipients. The preparation has a shape and material consistency to be contained in the swallowable capsule, delivered from the capsule into the lumen wall and degrade within the lumen wall to release the dose of therapeutic agent. Typically, this shape and material consistency are achieved by placing or forming the preparation into one or more embodiments of the tissue penetrating members described herein. The preparation may also have a selectable surface area to volume ratio so as enhance or otherwise control the rate of degradation of the preparation in the wall of the small intestine or other body lumen. The dose of the drug or other therapeutic agent in the preparation can be titrated downward from that which would be required for conventional oral delivery methods so that potential side effects from the drug can be reduced.

In another aspect, the invention provides methods for the delivery of drugs and the therapeutic agents into the walls of a patient's gastric antrum and other regions of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection due to chemical breakdown in the stomach e.g., growth hormone, parathyroid hormone, insulin, interferons (for treatment of MS and other conditions) and other like compounds. Suitable drugs and other therapeutic agents which can be delivered by embodiments of invention include various antibodies (e.g., HER 2 antibodies), chemotherapeutic agents (e.g., interferon), insulin and related compounds for treating diabetes, glucagon like peptides (e.g., .GLP-1, exenatide), parathyroid hormones, growth hormones (e.g., IFG and other growth factors), immune suppression agents (e.g., cyclosporines, cortisones, etc.), vaccines and anti-parasitic agents such as various antimalarial agents. In specific embodiments, embodiments of the swallowable capsule can be used to delivery therapeutically effective amounts of the monoclonal antibody adalimumab for the treatment of various autoimmune related disorders such as rheumatoid arthritis. The dosage of this or particular therapeutic agent can be titrated for the patient's weight, age, condition or other parameter.

In various method embodiments of the invention, embodiments of the swallowable drug delivery device can be used to deliver a plurality of drugs for the treatment of multiple conditions or for the treatment of a single condition, particularly those for which treatment requires or benefits from the delivery of multiple drugs (e.g., a mixture of protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc., drugs can be absorbed through the intestinal wall at different rates, resulting in different pharmacokinetic distribution curves. Embodiments of the invention address this issue by injecting the desired drug mixtures at about the same time. This in turn, improves the pharmacokinetics and thus, the efficacy of the selected mixture of drugs.

Further details of these and other embodiments and aspects of the invention are described more fully below, with reference to the attached drawing figures.

BRIEF DESCRIPTION OF THE DRAWINGS

FIGS. 5A-1 to 5F-2 illustrate processing of a swallowable capsule in a patient's gastric antrum which results in injection of a therapeutic agent into an antral wall, as shown in FIGS. 5D-1 and 5D-2.

DETAILED DESCRIPTION

Embodiments of the invention provide devices, systems and methods for delivering drugs, substances, medications, and the like into an antral wall or other locations in the body. As used herein, the terms "therapeutic agent,' "medicament," medication," and "drug" are used interchangeably and refer to any medicinal preparation intended as a therapeutic, diagnostic, or other biologically active purpose in any form which can include drugs or other therapeutic agents as well as one or more pharmaceutical excipients. Many embodiments of the invention provide a swallowable device for delivering medication within the gastric antrum GA or other regions of the GI tract. Particular embodiments provide a swallowable device such as a capsule, for delivering medications into the wall of the antrum in response to pressure exerted on the capsule by contractions of the antrum.

The devices, systems, and methods of the present invention are particularly suited for delivering drugs to particular regions within a GI tract including for example portions of the stomach wall such as the antrum wall. Further they are also suited to delivering drugs into the antrum wall even when partially digested food is present in the stomach. After beginning the digestive process in the body of the stomach, the partially digested food enters the Fundus or body of the stomach then passes into the gastric antrum. It is in the gastric antrum GA (also referred to as antrum A) where the devices and methods of the present invention will preferably deliver a therapeutic agent into a wall of the antrum. After delivering the therapeutic agent, the devices will pass through the pyloric sphincter PS and into the duodenum D from where the intact, partially degraded, or fully degraded device passes through the large intestines and be excreted from the body.

Figure 1A:
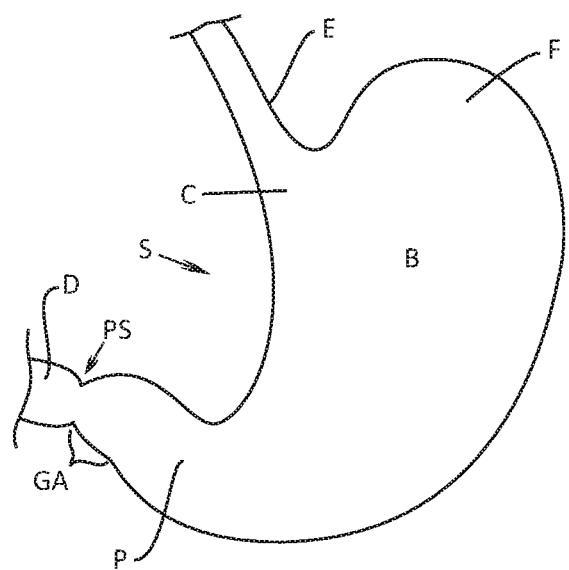
FIG. 1A illustrates regions of a patient's gastrointestinal (GI) tract, and in particular, the stomach, relevant to the devices and methods of the present invention.
Figure 1B:
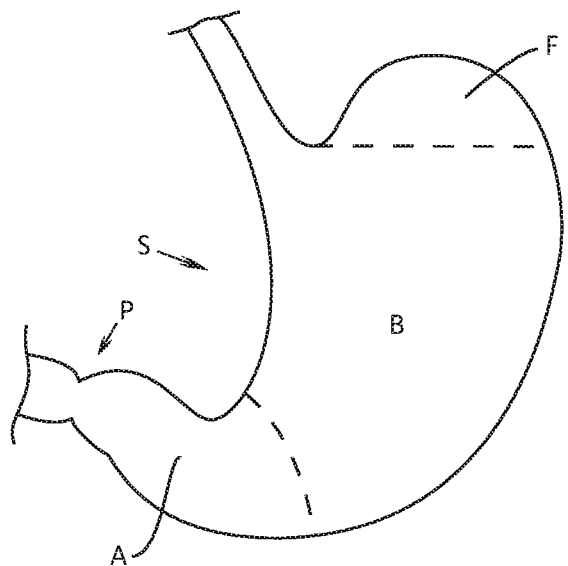
FIG. 1B illustrates the anatomical regions of a patient's stomach.
Figure 1C:
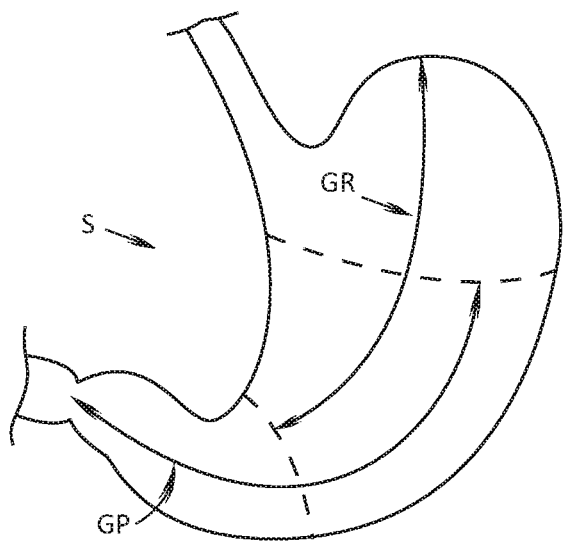
FIG. 1C illustrates the functional regions of a patient's stomach.

As many embodiments of the invention contemplate delivery of drugs and other therapeutic agents into walls of the GI tract including walls of the gastric antrum, a brief description will now be provided on the anatomy and function of the GI tract including the stomach. As shown in FIG. 1A, the GI tract begins with the esophagus E and enters the stomach S at the cardia C. Food thus enters the stomach through the esophagus after passing through the cardia. As shown in FIG. 1B, the major anatomic regions of the stomach include the fundus F, the corpus or body B, the antrum (A) and pylorus P. While the wall of the fundus is thin, the wall of the antrum is much thicker (due to a muscular layer) easily allowing for delivery of an embodiment of solid drug dose described here. However, the functional regions of the stomach do not correspond to the anatomic regions. As shown in FIG. 1C, functionally, the stomach can be divided into the gastric reservoir GR and the gastric pump GP. The gastric reservoir includes the fundus F and corpus or Body B. The gastric pump is represented by the area at which peristaltic waves occur: it includes the distal part of the corpus and the antrum. Due to different properties of the smooth muscle cells the gastric reservoir is characterized by tonic activity and the gastric pump by phasic activity known as peristaltic waves. The main feature of the gastric pump is the peristaltic wave. It originates at the proximal stomach and propagates to the pylorus. The peristaltic waves are based on electrical waves originating in the gastric wall. In the wall of both the stomach and small intestine, there is a network of interstitial cells—called interstitial cells of Cajal (ICC). These interstitial cells produce electrical pacesetter potentials due to oscillations in their membrane potential. The pacesetter potential of the ICCs drives electrical events in the smooth muscle cells where they are reflected by slow waves. The frequency of the pacesetter potentials and the resulting peristaltic contractions occur approximately three times a minute or about 20 seconds. The pacesetter potentials determine the maximal frequency and the propagation velocity of the peristaltic wave. In the region of the gastric corpus the peristaltic waves are shallow; they represent—as mentioned above—the pump of the gastric reservoir. When the peristaltic wave reaches the antrum (A), the circular constriction of the antrum becomes deeper such that the antrum develops into tubular shape in which force is applied to the contents of the antrum. The emptying mechanism of the antral pump can be divided into three phases: 1) a phase of propulsion, 2) a phase of emptying and mixing, and 3) a phase of retropulsion and grinding. A brief explanation will now be provided of the three phases. When the peristaltic wave moves over the proximal antrum the previously contracting terminal antrum relaxes. This results in the chyme and other stomach contents being propelled into the distal (or terminal) antrum which corresponds to propulsion phase). When the peristaltic wave moves over the middle of the antrum, the pylorus opens and duodenal contractions are inhibited; thus, small amounts of gastric chyme are delivered across the pylorus into the duodenum. During this phase of emptying and mixing, the peristaltic waves are relatively far away from the pylorus, i.e. the gastric chyme is not forced into the duodenum by pressure but is swept into the small intestine by the peristaltic wave. This mechanism of the antral pump is associated with a sieving effect. In particular, the shape of the antrum becomes tubular allowing for flow of liquid and small particles from the pylorus into the duodenum whereas more solid matter including embodiments of swallowable capsule 10 are retained in the antrum by being blocked by the relatively small opening of the pylorus. When so retained during this this phase of antral contractions, the forces of the contracting antrum are applied to the surface of the capsule where they may be sensed using a pressure or other sensor 12 described below.

Figure 2A:
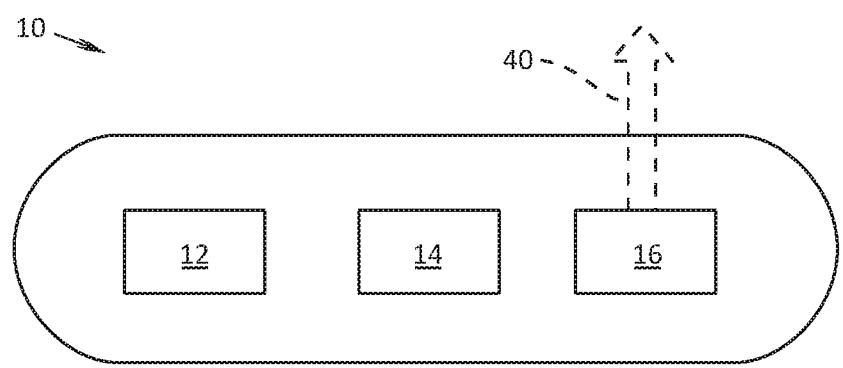
FIG. 2A illustrates the principal components of a swallowable drug delivery device constructed in accordance with the principles of the present invention.

According to one or more embodiments, a swallowable capsule or other swallowable device 10 for delivery of a therapeutic agent into a lumen wall of the GI tract may include a pressure or other proximity sensor 12, a driver 14, and a drug dosage 16 to be delivered, as shown in FIG. 2A. The nature of these specific components can vary widely, depending on the mode of drug delivery and the target drug delivery region within the GI tract. For example, the pressure or other proximity sensor 12 may be mechanical, electrical, or combinations thereof depending upon whether the device 10 is intended to deliver in the stomach or small intestine. The sensor 12 will typically be able to sense force/pressure applied externally to the swallowable capsule 10, and in particular will be able to sense when pressure is being applied to the exterior of the capsule by contractions of the antrum. It will be appreciated that the pressure applied by the antrum is unique within the GI tract and sensing of pressures exceeding a minimum threshold value may be relied upon to indicate that the swallowable capsule 10 has reached the interior of the antrum.

The driver 14 may also have any one of a variety of forms. Also, they may rely on mechanical, electrical, chemical or other stored energy in order to initiate release of the therapeutic agent from the capsule as indicated by the broken arrow shown in FIG. 2A. The driver 14 will be coupled to the pressure or other proximity sensor 12 so that the driver will be actuated in response to the pressure sensor sensing a pressure above the predetermined threshold value, indicating that the swallowable capsule 10 has reached the interior of the patient's antrum. In some instances, the sensor and the driver may be configured to convert the pressure applied by contractions of the gastric antrum into a force that drives the drug into the antral wall.

Figure 3:
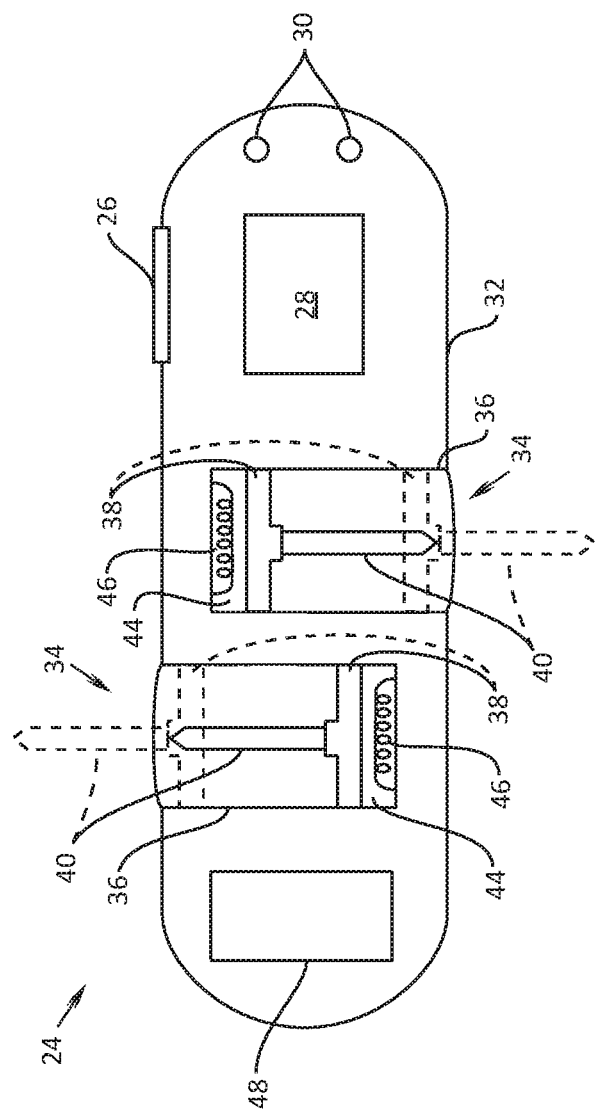
FIG. 3 illustrates the principal components of a particular embodiment of a swallowable drug delivery device constructed in accordance with the principles of the present invention.

Referring now to FIG. 3, a particular embodiment of a swallowable capsule 24 having the operative components of the present invention is shown in more detail. A solid state pressure sensor 26, such as a solid state piezoelectric element, is typically mounted in an external wall of the capsule. According to specific embodiments the pressure sensor 26 or other proximity sensor 12 may positioned in close proximity (1 to 5 mm) to where the solid drug dosage 40 (e.g., a issue penetrating member TPM) exits the capsule 24 (e.g. where cylinders 36 are positioned in the capsule) so that there can be increased assurance that the antrum wall is indeed in contact with the capsule surface when driver 14 is triggered to eject that solid drug dosage into the antrum wall. In this way, there is increased reliability that the solid drug dosage 40 is delivered into the antral wall or other desired location in the stomach, or other portion of the GI Tract. The pressure sensor 26 is connected to a control module 28 (also referred to herein in as a controller 28) in the interior of the capsule. The control module 28 will typically comprise or include a microprocessor (and associated software executable on the processor) configured to control all (or a portion of the) operations of the swallowable capsule 24, as described in more detail below. In alternative or additional embodiments, control module 28 may also correspond to an analogue device as well. In some embodiments, the swallowable capsule 24 will also have fluid or other sensors 30 to confirm when the swallowable has been swallowed and is in the stomach so as turn on capsule power to begin sensing pressure by pressure sensor. According to one or more embodiments fluid sensors 30 may correspond to electrodes disposed on the capsule surface or other location on the capsule which sense conductive bridging between the electrodes by digestive fluids in the stomach, to confirm when the capsule has entered the stomach. In use, fluid sensors 30 serve to conserve power of the battery or other electrical power source 48 so that the capsule only begins to expend power to sense applied pressure to the capsule by surface after the capsule has been swallowed.

The swallowable capsule 24 is surrounded by capsule wall 32 enclosing an interior which holds a pair of drug delivery modules 34. Each drug delivery module 34 includes a cylinder 36 having a reciprocating piston 38 therein. The piston 38 is initially retracted, as shown in FIG. 3, having a space adjacent a bottom of the associated cylinder 36. The space may be filled with a chemical propellant 44 and may have a coil or other igniter 46 therein. In this way, the control module 28 may electrically ignite the propellant 44, driving solid dosage drugs 40 in the directions shown in broken line in FIG. 3. The swallowable capsule 24 will typically also carry a chemical storage battery (e.g., a lithium battery) or other electrical power source 48 in order to power the control module 28, igniters 46, and other components. In some embodiments, electrical power source 48 may correspond to a capacitor. In particular embodiments where the driver corresponds to nitrocellulose or other ignitable chemical propellant, which is ignited by ignitor(s), the ignitor may have its own dedicated power source 48' which will typically correspond to a capacitor configured to provide sufficient current and voltage to ignite ignitor 46.

Drug dosage 16 may have a variety of forms including solid, liquid, powder, gel and combinations thereof. In many embodiments at least a portion of dosage 16 will be in solid form and/or carried by a solid carrier. Typically, the solid form of drug dosage 16 and/or its carrier are self-penetrating, often having sharpened, honed, or other tissue-penetrating tips. In many embodiments such self-penetrating forms of dosage 16 and/or its carrier are in the form of a tissue penetrating member 40. Details of tissue penetrating member 40 and other such solid dosage forms 16 of therapeutic agent are provided in more detail below.

Figure 4:
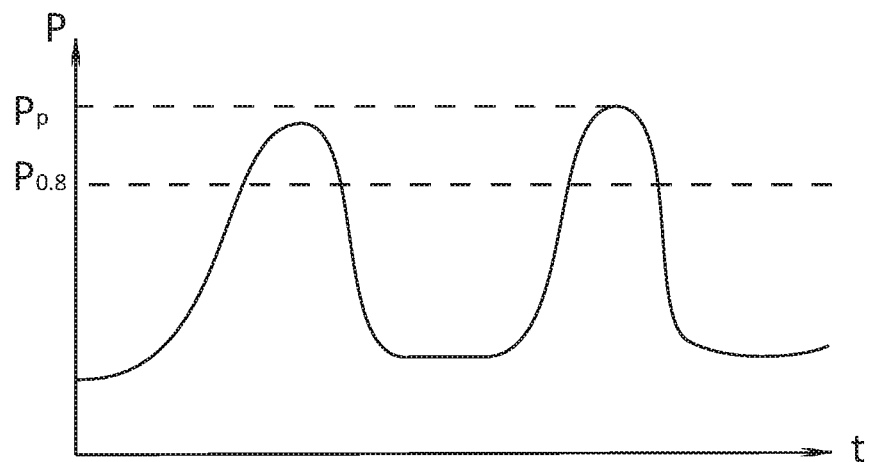
FIG. 4 is a graph illustrating a typical pressure profile in a patient's gastric antrum during normal digestive processing of food.
Figure 2B:
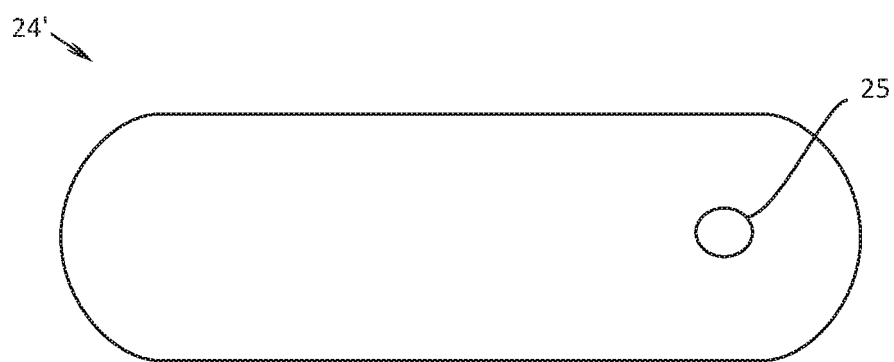
FIG. 2B illustrates a test capsule for measuring pressure in a patient's GI tract.

According to particular embodiments, the pressure sensor 26 and control module 28 may be configured and programmed to sense changes in the external pressure/force applied to the capsule wall by peristalsis of the antral wall known as antral peristalsis. Antral peristalsis typically comprises a series of pressure waves, as shown in FIG. 4, having a peak pressure $P_p$. Particular peak pressure values may be determined for a patient population and/or for a particular patient, and a pressure value may be selected which is less than the peak pressure at which to initiate therapeutic preparation delivery from the swallowable capsule 24. For example, the trigger pressure may be 80% of the peak pressure value, as shown at $P_{0.8}$, in FIG. 4. It is contemplated that other trigger pressure values may be selected (e.g. 70, 85, 90% etc. of peak Pressure $P_p$). As described according to some embodiments, the peak pressure may be determined by configuring the capsule to be retained in the antrum for several peristaltic contractions of the antrum and configuring the controller 28 and or control module to record applied antral pressures through several cycles of peristaltic contraction and then calculate average peak pressure as well as other information related to antral peristaltic contraction including average frequency and period of contraction. According to some embodiments, the patient may first swallow a test capsule or capsule mimic 24' (FIG. 2B) that does not necessarily contain a driver 14 and therapeutic agent 40, but rather whose primary function is to record the applied pressure to the capsule 24' through a number of antral peristaltic contractions (or peristaltic contractions in other locations of the GI tract) and then calculate and transmit to an external device (e.g., a cell phone or tablet) various information related to those contractions including one or more of average peak peristaltic pressure, frequency and period of contraction and the like. Typically the test capsule 24' will have a pressure or related sensor 25 positioned on or operably coupled to its outer surface for measuring such pressure data and internal circuitry (not shown) for recording and/or transmitting the observed pressure data as the test capsule 24' travels through the GI tract. That acquired data or information can then be inputted from the external device to a control module 28 (e.g., a processor or other logic means) incorporated into or otherwise associated with capsule 24 and then be utilized to trigger, modify or otherwise control the release of therapeutic agent into the antral wall. In these and related embodiments, the control module 28 may include or otherwise by operatively coupled to memory means (e.g., ram, dram, volatile memory etc.) for storing the acquired data and/or application software executable on the controller/processor in the operation of the device, as well as transmission means such as an RF transmission device known in the art. In particular embodiments, the RF transmission/transceiver device may be configured to use a BLUE TOOTH communications protocol so as to communicate with an external device such as cell phone, tablet and the like Referring now to FIGS. 5A-1 through 5F-2, the delivery of a swallowable capsule 10 to an antral wall in accordance with the principles of the present invention will be described. Initially, the gastric antrum GA is empty while the antral wall AW is undergoing peristaltic contractions and thus constrictions, as shown in FIGS. 5B-1 and 5B-2. The patient then ingests a swallowable capsule 10, and the capsule eventually approaches the gastric antrum GA as shown in FIGS. 5C-1 and 5C-2. As the swallowable capsule 10 enters the gastric antrum GA, the gastric walls will constrict over its exterior, as shown in FIGS. 5D-1 and 5D-2. The pressure/force exerted by the antral wall AW on the exterior of the capsule 24 is then sensed by pressure/force sensor 26, causing (e.g., through use of control module 28) the solid dosage forms 40 to be released through the wall of the capsule and into the antral wall AW, as shown in FIGS. 5D-1 and 5D-2.

In particular implementations, the control module 28 or other circuitry can be configured to measure and store the pressure/force vs time curves from several peristaltic contractions of the antrum wall in order to develop a database of pressure/force curves of antral contractions for an individual patient particularly occurring during one or more phases the antral pump described above. Further as described below, various information including parameters such as peak peristaltic pressure/force (or a selected of peak pressure e.g. 80%) applied to the capsule and frequency and/or period of peristaltic contractions of the antrum may be derived from the pressure/force curves by control module 28 or logic means. In various embodiments one or a combination of both of these or other parameters may be used by control module 28 to trigger the release of tissue penetrating member 40 into the antrum wall. In a particular approach, the control module 28 can be configured to use both a selected percentage of peak contractile pressure and a selected period of contraction to trigger release of tissue penetrating member 40. In using one or more of these approaches, the capsule is better able to sense when a peristaltic wave/contraction occurs of the antrum (or other GI wall) which results in a desired amount of contraction and/or contact of the antrum on the capsule 10. In this way, the reliability of the delivery of the tissue penetrating member 40 (or other form of drug dosage 16) into the antral wall (or other portion of the stomach or GI tract) is significantly improved.

In various embodiments, the capsule 24 may be desirably sized and shaped or otherwise configured to remain in the antrum during several peristaltic contractive phases of the antral pump so that it may sense and record multiple peristaltic contractions of the antrum so as derive information of the antral contractions unique to a particular patient including average peak antral peristaltic pressure applied to the capsule as well as the frequency and/or period of antral peristaltic contractions. This can be accomplished through various approaches. For example, according to one approach, the diameter of capsule 24 can be sized such that it is somewhat larger than that of the only the partially opened pyloric sphincter. In additional or alternative embodiments, the capsule 24 can be configured to remain in the antrum during peristaltic contractions which might otherwise force it out of the antrum A or sphincter PS through the use of various surface coatings or surface features for enhancing or improving the grip or hold of the antrum on the wall 32 of capsule 24 during contraction of the antrum or other portion of the stomach or GI wall around at least a portion of the capsule. The coatings may include pressure activated bio-adhesive coatings, including pressure activated bio-adhesives having weak adhesive forces known in the art. Such surface features may include various texturized surfaces known in the art including knurled surfaces which increase the coefficient of friction between the surface of the antrum and the capsule surface when the capsule is gripped by the antrum, thus increasing the amount of force required to force the capsule distally out of the antrum and/or reducing movement of the capsule within antrum during a peristaltic or other contraction of the antrum or other GI wall. In use, such surface coatings or features improve the reliability of advancement of tissue penetrating member 40 (or other carrier or form of drug dosage 16) into the antrum wall during a peristaltic contraction.

The antral wall will continue to undergo peristalsis, eventually releasing the swallowable capsule 10 as shown in FIGS. 5E-1 and 5E-2. The capsule 10, if it hasn't completely degraded, will then pass through the Pyloric Sphincter PS (also described as Pyloric Valve PS) and into the Duodenum D, as shown in FIGS. 5F-1 and 5F-2. After passing through the Pyloric Sphincter PS and into the Duodenum D, eventually capsule 10 be excreted from the patient.

Referring back to FIG. 3, in various embodiments, swallowable capsule 24 including tissue penetrating member 40 can be configured for the delivery of liquid, semi-liquid or solid forms of medication or combinations of all three. Whatever the form, the medication desirably has a material consistency allowing the medication to be advanced out of swallowable capsule 24, into a target location on the antral or other GI wall (e.g., the small intestine) and then degrade within the wall to release the drug or other therapeutic agent into the wall and/or surrounding tissue and in turn into the patient's blood stream. The material consistency of the medication can include one or more of the hardness, porosity and solubility of the preparation (in body fluids). The material and dimensions of the tissue penetrating member or other drug dosage 40 may also be optimized for the particular target location in the GI tract. For example, for delivery into the antral wall longer tissue penetrating members may be used with greater degree of hardness in order to penetrate the more muscular portions of the antrum wall. The material consistency can be achieved by selection and use of one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art.

Swallowable capsule 24 is sized to be swallowed and pass through the GI tract at least to the antrum. However, in particular embodiments the diameter of the capsule can be sized such that it is retrained in the antrum when the pyloric sphincter is only partially opened. The size can also be adjusted depending upon the amount of drug to be delivered as well as the patient's weight and adult vs. pediatric applications. In additional or alternative approaches, the capsule may also include surface coatings and features described herein to help retain the capsule in the antrum when pyloric sphincter is only partially opened. Typically, the capsule will have a tubular shape with curved ends similar to a vitamin. In these and related embodiments, capsule lengths can be in the range of 0.5 to 2 inches with diameters in the range of 0.1 to 0.5 inches with other dimensions contemplated. The swallowable capsule 24 includes a capsule wall 32, having an exterior surface and an interior surface defining an interior space or volume. In some embodiments, the capsule wall can include one or more apertures sized for the outward advancement of tissue penetrating members 40.

The swallowable capsule 24 will typically, but not necessarily, be fabricated from a biodegradable material, such as a gelatin as known in the pharmaceutical arts, and may include an enteric coatings configured to protect the capsule from degradation in the stomach and antrum (due to acids etc.), and then subsequently degrade in the in higher pH's found in the small intestine or other area of the intestinal tract. In various embodiments, the swallowable capsule 24 can be formed from multiple portions or segments (e.g. two halves) one or more of which may be biodegradable.

As is discussed above, one or more portions of capsule 24 can be fabricated from various biocompatible polymers known in the art, including various biodegradable polymers which in a preferred embodiment can comprise cellulose, gelatin materials PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

Use of biodegradable materials for swallowable capsule 24, including biodegradable enteric materials allows the capsule to degrade in whole or part to facilitate passage through the GI system before, during or after drug delivery. As is described in further detail herein, in various embodiments, swallowable capsule 24 can include seams 22 of bio-degradable material so as to controllably degrade into smaller pieces 23 which are more easily passed through the intestinal tract.

In various embodiments, swallowable capsule 24 can include various radio-opaque, echogenic or other materials for location of the device using one or more medical imaging modalities such as fluoroscopy, ultrasound, MM, etc. In specific embodiments, all or a portion of the capsule can include radio-opaque/echogenic. Suitable materials for radio-opaque markers include barium sulfate, compounds, titanium dioxide and compounds thereof. In use, such materials allow for the location of swallowable capsule 24 in the GI tract, as well as its state of deployment (e.g., a distinctive marker can be positioned on each end and optionally elsewhere on the wall 32) allowing for visual confirmation that the swallowable capsule 24 has properly aligned in the antrum prior to release of the therapeutic agent. They can also be used allow for the determination of transit times of the device through the GI tract. Such information can be used to titrate dosages of drug for a particular patient, as well as provide information on when they should take a particular drug after an event such as ingestion of a meal, e.g. in the case of insulin taken for treatment of diabetes.

Tissue penetrating members 40 can be fabricated from various drugs and other therapeutic agents, one or more pharmaceutical excipients (e.g., disintegrants, stabilizers, etc.), and one or more biodegradable materials (e.g., PEO) which may be used to form the main structural component of a TPM including a shaft having a tip as discussed below and described in detail in U.S. Pat. Nos. 9,757,548; 8,562, 589; 8,809,269; 8,969,293; 8,809,271; 8,980,822; 9,861, 683; 9,259,386; 9,284,367; 9,149,617; 8,734,429; 9,283, 179; 8,764,733; 9,402,806; 9,629,799; 9,415,004; 9,402, 807; 8,846,040; 10,098,931; and 10,220,003; and U.S. application Ser. Nos. 15/144,733; 15/150,379; 15/260,260; 15/928,606; 16/183,573; and provisional application No. 62/786,831, having common inventorship with the present application, the full disclosures of which are incorporated herein by reference for all purposes.

Specific materials can be chosen to confer desired structural and material properties to the penetrating member (for example, column strength for insertion into the stomach or intestinal wall, or porosity and hydrophilicity for controlling disintegration of the penetrating member and thus the release of drug). In many embodiments, the penetrating member 40 can be formed to have a shaft and a needle tip or other pointed tip so as to readily penetrate tissue of the antrum or other intestinal wall, as shown for example in FIGS. 5D-1 and 5D-2. In exemplary embodiments, the tip has a trocar and may comprise various degradable materials (within the body of the tip or as a coating), such as sucrose, maltose or other sugar that increase the hardness and tissue penetrating properties of the tip. Once placed in the intestinal wall, the penetrating member 40 is degraded by the interstitial fluids within the wall tissue so that the drug or other therapeutic agent dissolves in those fluids and is absorbed into the blood stream. One or more of the size, shape and chemical composition of tissue penetrating member 40 can be selected to allow for dissolution and absorption of an incorporated drug in a matter of seconds, minutes or even hours. Rates of dissolution can be controlled through the use of various disintegrants known in the pharmaceutical arts. Examples of disintegrants include, but are not limited to, various starches such as sodium starch glycolate and various cross linked polymers such as carboxymethyl cellulose. The choice of disintegrants can be specifically adjusted for the environment within the wall of the small intestine e.g., blood flow, average number of peristaltic contractions, etc.

Tissue penetrating member 40 may also typically include one or more tissue retaining features, such as a barb or hook to retain the penetrating member within the tissue of the antral or other region of the intestinal wall after advancement. Retaining features can be arranged in various patterns to enhance tissue retention such as two or more barbs symmetrically or otherwise distributed around and along member shaft. Additionally, in many embodiments, penetrating member may also include a recess or other mating feature for attachment to a coupling component on delivery mechanism. Such features are described in more detail in U.S. Pat. No. 8,734,429, which has previously been incorporated herein by reference.

Tissue penetrating member 40 is desirably configured to be detachably coupled to piston 38 so that after advancement of the tissue penetrating member 40 into the antral wall, the tissue penetrating member detaches from the piston. Detachability can be implemented by a variety of means including: i) the snugness or fit between an opening in the piston; ii) the configuration and placement of tissue retaining features on the tissue penetrating member 40 which anchor the tissue penetrating member is tissue to promote detachment from the piston; and iii) the depth of penetration of the tissue penetrating member into the intestinal wall. Using one or more of these factors, tissue penetrating member 40 may be configured to detach as the piston is retracted or otherwise pulls back away from the antral wall and/or the forces exerted on swallowable capsule 24 by a peristaltic contraction or other contractions of the antrum.

As described above, in various embodiments, tissue penetrating member 40 can be fabricated from a number of drugs and other therapeutic agents. Also, according to one or more embodiments, the tissue penetrating member may be fabricated entirely from drug or may have other constituent components as well, e.g., various pharmaceutical excipients (e.g., binders, preservatives, disintegrants, etc.), polymers conferring desired mechanical properties, etc. Further, in various embodiments, one or more tissue penetrating members 40 can carry the same or a different drug (or other therapeutic agent) from other tissue penetrating members. The former configuration allows the delivery of greater amounts of a particular drug, while the later allows two or more different drugs to be delivered into the antral wall at about the same time to facilitate drug treatment regimens requiring substantial concurrent delivery of multiple drugs.

Typically, the drug or other therapeutic agent carried by the tissue penetrating member 40 will be mixed in with a biodegradable material to form tissue penetrating member 40. The biodegradable material may include one or more biodegradable polymers such as PEO (polyethylene oxide), PGLA, cellulose, as well as sugars such as maltose or other biodegradable material described herein or known in the art. In such embodiments, the penetrating member 40 may comprise a substantially heterogeneous mixture of drug and biodegradable material. Alternatively, the tissue penetrating member 40 may include a portion formed substantially from biodegradable material and a separate section that is substantially formed from or contains drug, herein described as a drug section. Such separate drug sections may comprise shaped sections which may be pre-formed as a separate section which is then inserted into a cavity in tissue penetrating member 40 to allow for a modular fabrication. Alternatively, drug and/or a drug preparation may be introduced into to cavity(ies) in the tissue penetrating member 40, e.g. by being combined as a powder, liquid, or gel which is poured or injected into a cavity, well, hollow interior, or other receptacle in the tissue penetrating member 40. Shaped section 42s may be formed of drug by itself or a drug preparation containing drug and one or more binders, preservatives, disintegrates and other excipients.

In various embodiments, the weight of tissue penetrating member 40 can range between about 10 to 15 mg, with larger and smaller weights contemplated. For embodiments of tissue penetrating member 40 fabricated from maltose, the weight can range from about 11 to 14 mg, while for PEO the weight of the tissue penetrating member can in be in the range of 10 to 15 mg. In various embodiments, depending upon the drug and the desired delivered dose, the weight percent of drug in member 40 can range from about 0.1 to about 15%. The weight percent of drug in member 40 can be adjusted depending upon the desired dose as well as to provide for structural and stoichiometric stability to the drug and also to achieve a desired elution profile of the drug. Table 1 lists the dose and weight percent range for a number of drugs which may be delivered by tissue penetrating member 40.

TABLE 1

| Drug | Dose Via Capsule** | % Weight of Drug in the needle |
|---|---|---|
| Insulin | 5-30 Units | 2-15% |
| Exenatide | 10 ug | <1% |
| Liraglutide | 0.6 mg | 3-6% |
| Pramlintide | 15-120 ug | 0.1-1% |
| Growth Hormone | 0.2-1 mg | 2-10% |
| Somatostatin | 50-600 ug | 0.3-8% |
| GnRH and Analogs | 0.3-1.5 mg | 2-15% |
| Vasopressin | 2-10 units | <1% |
| PTH/Teriparatide | 20 ug | 1-2% |
| Interferons and analogs | | |
| 1. For Multiple Sclerosis | 0.03-0.25 mg | 0.1-3% |
| 2. For Hep B and HepC | 6-20 ug | 0.05-0.2% |
| Adalimumab | 2-4 mg/day | 8-12% |
| Infliximab | 5 mg/day | 8-12% |
| Etanercept | 3 mg/day | 8-12% |
| Natalizumab | 3 mg/day | 8-12% |

Tissue penetrating member 40 can be fabricated using one or more polymer and pharmaceutical fabrication techniques known in the art. For example, drug (with or without a biodegradable material) can be in solid form and then formed into the shape of the tissue penetrating member 40 using molding, compaction or other like method with one or more binding agents added. Alternatively, drug and/or drug preparation may be in solid or liquid form and then added to the biodegradable material in liquid form with the mixture then formed into the penetrating member 40 using molding or other forming method known in the polymer arts.

Desirably, embodiments of the tissue penetrating member 40 comprising a drug or other therapeutic agent and degradable material are formed at temperatures which do not produce any substantial thermal degradation of the drug (or other therapeutic agent) including drugs such as various peptides and proteins. This can be achieved through the use of room-temperature curing polymers and room temperature molding and solvent evaporation techniques known in the art. In particular embodiments, the amount of thermally degraded drug or other therapeutic agent within the tissue penetrating member is desirably less than about 10% by weight and more preferably, less than 5% and still more preferably less than 1%. The thermal degradation temperature(s) for a particular drug are either known or can be determined using methods known in the art and then this temperature can be used to select and adjust the particular polymer processing methods (e.g., molding, curing. solvent evaporation methods etc.) to minimize the temperatures and associated level of drug thermal degradation.

After medication delivery, swallowable capsule 24 (including some or all of the pressure sensor 26, the control module 28, and the drug delivery modules 34) can pass from the antrum through the intestinal tract including the small and large intestine and be ultimately excreted. For embodiments of the capsule 24 having biodegradable seams or other biodegradable portions, the capsule is degraded in the intestinal tract into smaller pieces, to facilitate passage through and excretion from the intestinal tract. In particular embodiments having biodegradable tissue penetrating needles/members 40, should the needle get stuck in the wall of the stomach, intestine (small or other large) or other location in the GI tract, the needle will biodegrade, releasing the capsule 24 from the stomach or intestinal wall.

One or more embodiments of the above methods can be used for the delivery of preparations containing therapeutically effective amounts of a variety of drugs and other therapeutic agents to treat a variety of diseases and conditions. These include a number of large molecule peptides and proteins which would otherwise require injection due to chemical degradation and/or deactivation in the stomach or intestines including, e.g., antibodies including various monoclonal antibodies such as tnf alfa antibodies, growth hormone, parathyroid hormone, insulin, interferons and other like compounds. Suitable drugs and other therapeutic agents which can be delivered by embodiments of the invention include various immunochemical agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents (e.g., Furosemide), antimigraine medication (sumatriptan), immune suppression agents (e.g., cyclosporine) and anti-parasitic agents such as various anti-malarial agents. The dosage of the particular drug can be titrated for the patient's weight, age or other parameter. Also the drug to achieve a desired or therapeutic effect (e.g., insulin for blood glucose regulation, Furosemide for anti-seizure) can be less than the amount required should the drug have been delivered by conventional oral delivery (e.g., a swallowable pill that is digested in the stomach and absorbed through the wall of the small intestine). This is due to the fact that there is no degradation of the drug by acid and other digestive fluids in the stomach and the fact that all, as opposed to only a portion of the drug is delivered into the wall of the small intestine (or other lumen in the gastrointestinal tract, e.g., large intestine, stomach, etc.). Depending upon the drug, the dose delivered in preparation can be in the range from 5% to 100% of a dose delivered by conventional oral delivery means to achieve a desired therapeutic effect (e.g., blood glucose regulation, seizure regulation, etc.) with even lower amounts contemplated. The particular dose reduction can be titrated based upon the particular drug, the condition to be treated, and the patient's weight, age and condition. For some drugs (with known levels of degradation in the intestinal tract) a standard dose reduction can be employed (e.g., 10 to 20%). Larger amounts of dose reduction can be used for drugs which are more prone to degradation and poor absorption. In this way, the potential toxicity and other side effects (e.g., gastric cramping, irritable bowel, hemorrhage, etc.) of a particular drug or drugs delivered by swallowable capsule 24 can be reduced because the ingested dose is lowered. This in turn, improves patient compliance because the patient has reduction both in the severity and incidence of side effects. Additional benefits of embodiments employing dose reduction of drug include a reduced likelihood for the patient to develop a tolerance to the drug (requiring higher doses) and, in the case of antibiotics, for the patient to develop resistant strains of bacteria. Also, other levels of dose reduction can be achieved for patients undergoing gastric bypass operations and other procedures in which sections of the small intestine have been removed or its working (e.g., digestive) length effectively shortened.

In addition to delivery of a single drug, embodiments of swallowable drug delivery swallowable capsule 24 and methods of their use can be used to deliver into antrum wall or other location in the GI tract a plurality of drugs for the treatment of multiple conditions or for the treatment of a particular condition (e.g., protease inhibitors for treatment HIV AIDs). In use, such embodiments allow a patient to forgo the necessity of having to take multiple medications for a particular condition or conditions. Also, they provide a means for facilitating that a regimen of two or more drugs is delivered and absorbed into the small intestine (or surrounding tissue) and thus, the blood stream, at about the same time. Due to difference in chemical makeup, molecular weight, etc., drugs can be absorbed through the intestinal wall at different rates, resulting in different pharmacokinetic distribution curves. Embodiments of the invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations including drugs and other therapeutic agents to provide treatment for a number of medical conditions and diseases. The medical conditions and diseases which can be treated with embodiments of the invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia's (both atrial and ventricular), coronary ischemia anemia or other like condition. Still other conditions and diseases are also contemplated such as various autoimmune disorders including multiple sclerosis, guillian barre syndrome, ankylosing spondylitis, chronic inflammatory demyelinating polyneuropathy, multifocal motor neuropathy, lupus and other like conditions. Therapeutic agents for the latter conditions may include IgG and rituximab.

In many embodiments, the treatment of the particular disease or condition can be performed without the need for injecting the drug or other therapeutic agent (or other non-oral form of delivery such as suppositories) but instead, relying solely on the therapeutic agent(s) that is delivered into the wall of the antrum, small intestine or other portion of the GI tract. For example, diabetes or another glucose regulation disorder can be treated (e.g., by controlling blood glucose levels) solely through the use of insulin that is delivered into the wall of the antrum, small intestine without the need for the patient to ever inject insulin. Similarly, the patient need not take conventional oral forms of a drug or other therapeutic agent, but again rely solely on delivery into the wall of the antrum or small intestine using embodiments of the swallowable capsule. In other embodiments, the therapeutic agent(s) delivered into the wall of the small intestine can be delivered in conjunction with an injected dose of the agent(s). For example, the patient may take a daily dose of insulin or compound for blood glucose regulation using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods can be used to determine the appropriate dosages). Also, for embodiments using therapeutic agents that can be delivered by conventional oral means, the dose delivered using embodiments of the swallowable capsule can be titrated below the dosage normally given for oral delivery of the agent since there is little or no degradation of the agent within the stomach or other portion of the intestinal tract (herein again standard dose response curve and other pharmacokinetic methods can be applied).

Various groups of embodiments of preparations containing one or more drugs or other therapeutic agents for the treatment of various diseases and conditions will now be described with references to dosages. It should be appreciated that these embodiments, including the particular therapeutic agents and the respective dosages are exemplary and the preparation can comprise a number of other therapeutic agents described herein (as well as those known in the art) that are configured for delivery into a luminal wall in the intestinal tract (e.g., the small intestinal wall) using various embodiments of swallowable capsule 24. The dosages can be larger or smaller than those described and can be adjusted using one or more methods described herein or known in the art. In one group of embodiments, therapeutic agent preparation can comprise a therapeutically effective dose of insulin for the treatment of diabetes and other glucose regulation disorders. The insulin can be human or synthetically derived as is known in the art. In one embodiment, the preparation can contain a therapeutically effective amount of insulin in the range of about 1-10 units (one unit being the biological equivalent of about 45.5 µg of pure crystalline insulin), with particular ranges of 2-4, 3-9, 4-9, 5-8 or 6-7. The amount of insulin in the preparation can be titrated based upon one or more of the following factors (herein, then "glucose control titration factors"): i) the patient's condition (e.g., type 1 vs. type II diabetes; ii) the patients previous overall level of glycemic control; iii) the patient's weight; iv) the patient's age; v) the frequency of dosage (e.g., once vs. multiple times a day); vi) time of day (e.g., morning vs. evening); vii) particular meal (breakfast vs. dinner); viii) content/glycemic index of a particular meal (e.g., meals having a high fat/lipid and sugar content (which tend to cause a rapid rise in blood sugar and thus have a higher glycemic index) vs. low fat and sugar content that do not (and thus have a lower glycemic index)); and ix) content of the patient's overall diet (e.g., amount of sugars and other carbohydrates, lipids and protein consumed daily).

In another group of embodiments, therapeutic agent preparation can comprise a therapeutically effective dose of one or more incretins for the treatment of diabetes and other glucose regulation disorders. Such incretins can include glucacon-like peptides 1 (GLP-1) and their analogues, and gastric inhibitory peptide (GIP). Suitable GLP-1 analogues include exenatide, liraglutide, albiglutide and taspoglutide as well as their analogues, derivatives and other functional equivalents. In one embodiment preparation can contain a therapeutically effective amount of exenatide in the range of about 1-10 µg, with particular ranges of 2-4, 4-6, 4-8 and 8-10 respectively. In another embodiment, the preparation can contain a therapeutically effective amount of liraglutide in the range of about 1-2 mg (milligrams), with particular ranges of 1.0 to 1.4, 1.2 to 1.6 and 1.2 to 1.8 mg respectively. One or more of the glucose control titration factors can be applied to titrate the dose ranges for exenatide, liraglutide or other GLP-1 analogue or incretin.

In yet another group of embodiments, the therapeutic agent preparation can comprise a combination of therapeutic agents for the treatment of diabetes and other glucose regulation disorders. Embodiments of such a combination can include therapeutically effective doses of incretin and biguanide compounds. The incretin can comprise one or more GLP-1 analogues described herein, such as exenatide and the biguanide can comprise metformin (e.g., that available under the Trademark of GLUCOPHAGE manufactured by Merck Santé S.A.S.) and its analogues, derivatives and other functional equivalents. In one embodiment, preparation can comprise a combination of a therapeutically effective amount of exenatide in the range of about 1-10 µg and a therapeutically effective amount of metformin in a range of about 1 to 3 grams. Smaller and larger ranges are also contemplated with one or more of the glucose control titration factors used to titrate the respective dose of exenatide (or other incretin) and metformin or other biguanide. Additionally, the dosages of the exenatide or other incretin and metformin or other biguanide can be matched to improve the level of glucose control for the patient (e.g., maintenance of blood glucose within normal physiological levels and/or a reduction in the incidence and severity of instances of hyperglycemia and/or hypoglycemia) for extended periods of time ranging from hours (e.g., 12) to a day to multiple days, with still longer periods contemplated. Matching of dosages can also be achieved by use of the glucose control regulation factors as well as monitoring of the patient's blood glucose levels for extended periods using glycosylated hemoglobin (known as hemoglobin A1c, HbA1c, A1C, or Hb1c) and other bioanalytes and measurements correlative to long term average blood glucose levels.

In still yet another group of embodiments, the therapeutic agent preparation can comprise a therapeutically effective dose of growth hormone for the treatment of one or more growth disorders, as well as wound healing. In one embodiment, preparation can contain a therapeutically effective amount of growth hormone in the range of about 0.1-4 mg, with particular ranges of 0.1-1, 1-4, 1-2 and 2-4, with still larger ranges contemplated. The particular dose can be titrated based on one or more of the following: i) the particular condition to be treated and its severity (e.g., stunted growth, vs. wound healing); ii) the patient's weight; iii) the patient's age; and iv) the frequency of dosage (e.g., daily vs. twice daily).

In still yet another group of embodiments, the therapeutic agent preparation can comprise a therapeutically effective dose of parathyroid hormone for the treatment and/or prevention of osteoporosis or a thyroid disorder. In one embodiment, preparation can contain a therapeutically effective amount of parathyroid hormone in the range of about 1-40 µg, with particular ranges of 10-20, 20-30, 30-40 and 10-40 µg, with still larger ranges contemplated. The particular dose can be titrated based on one or more of the following: i) the particular condition to be treated and its severity (e.g., the degree of osteoporosis as determined by bone density measurements); ii) the patient's weight; iii) the patient's age; and iv) the frequency of dosage (e.g., daily vs. twice daily). Particular embodiments contemplate the delivery (e.g., daily) of a prophylactic dose of PTH for prevention of osteoporosis in middle age (e.g., 50+) or older patients including prevention of osteoporosis in post-menopausal women. Such prophylactic doses can in in the lower range for example 5-20 µg so as to reduce risk of osteosarcoma for long term administration of the drug.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. Also those skilled in the art will recognize, or be able to ascertain, using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further, for any positive recitation of an element, characteristic, constituent, feature, act, step or the like, embodiments of the invention specifically contemplate the exclusion of that element, value, characteristic, constituent, feature, act, step or the like. Hence, the scope of the present invention is not limited to the specifics of the described embodiments, but is instead limited solely by the appended claims.

What is claimed is:

1. A swallowable device for delivering a therapeutic agent preparation into an antrum wall of a patient's stomach, the device comprising:
   a swallowable capsule having a capsule wall, wherein the therapeutic agent preparation is held inside the capsule;
   a driver within the capsule configured to advance the therapeutic agent preparation through the capsule wall and into the wall of the antrum;
   a sensor operatively coupled to the capsule wall which senses when the capsule wall is being squeezed by a peristaltic contraction of the antrum; and
   a trigger operatively coupled to the sensor and the driver, wherein, when the sensor senses that the capsule is being squeezed by the peristaltic contraction of the antrum, the trigger is triggered quickly enough to cause the driver to advance the therapeutic agent preparation through the capsule wall and into the antrum wall while at least a portion of the capsule is being squeezed by the peristaltic contraction of the antrum.

2. The device of claim 1, wherein the capsule wall comprises a cylindrical shell.

3. The device of claim 1, wherein at least a portion of the capsule wall is degradable in the patient's intestinal tract.

4. The device of claim 3, wherein the at least a portion of the capsule wall degrades at a pH equal to or greater than about 6.5.

5. The device of claim 1, wherein at least a portion of the capsule wall is non-degradable in the patient's gastrointestinal tract.

6. The device of claim 1, wherein the driver comprises a propellant.

7. The device of claim 6, wherein the propellant comprises nitrocellulose.

8. The device of claim 1, wherein the driver comprises a balloon.

9. The device of claim 1, wherein the driver comprises a compressed spring.

10. The device of claim 1, wherein the driver is a first driver configured to drive the therapeutic agent preparation in a first direction, the device further comprising at least a second driver configured to drive the therapeutic agent preparation in a second direction that is different from the first direction.

11. The device of claim 10, wherein the first and second directions are diametrically opposed directions.

12. The device of claim 1, wherein the sensor comprises an electronic transducer which generates a pressure signal representative of external pressure on the capsule wall.

13. The device of claim 12, wherein the trigger comprises an electronic circuit which receives the pressure signal from the sensor and generates a trigger signal when the pressure exceeds a predetermined threshold force.

14. The device of claim 13, wherein the predetermined threshold force is in a range from about 300 to 1100 dynes/cm$^2$.

15. The device of claim 14, wherein the predetermined threshold force is in a range from about 300 to 900 dynes/cm$^2$.

16. The device of claim 14, wherein the predetermined threshold force is in a range from about 835 to 1086 dynes/cm$^2$.

17. The device of claim 1, wherein the sensor comprises a mechanical or fluidic pressure transducer which changes state in response to changes in external pressure on the capsule wall above a threshold force.

18. The device of claim 17, wherein the threshold force is in a range from about 300 to 1100 dynes/cm$^2$.

19. The device of claim 1, wherein the therapeutic agent preparation comprises a solid dosage form configured to be advanced into the antrum wall by the driver.

20. The device of claim 19, wherein the solid dosage form comprises the therapeutic agent preparation formed or mixed with at least one of an excipient or a binder into an elongate member having a tapered, sharpened, or honed tip.

21. The device of claim 1, wherein the therapeutic agent preparation comprises a liquid dosage form advanced into the antrum wall through a hollow needle by the driver.

22. A swallowable device for delivering a therapeutic agent preparation into an antrum wall of a patient's stomach, the device comprising:
   a capsule sized to pass through the patient's gastrointestinal tract, the capsule having a wall including opposed side portions and opposed end portions, the capsule having an elongated shape configured to longitudinally orient within an antrum of the stomach during a peristaltic contraction of the antrum such that one of the opposed side portions of the capsule wall is adjacent a wall of the antrum;

a therapeutic preparation in the capsule, the preparation comprising a therapeutic agent and shaped as a tissue-penetrating member;

a sensor disposed in one of the opposed side portions of the capsule wall, the sensor configured to sense a force applied by the antrum wall to the capsule corresponding to a peristaltic contraction of the antrum and to generate an output upon sensing said force; and ejection means operatively coupled to the tissue penetrating member and the sensor, wherein the ejection means ejects the tissue penetrating member from the capsule into antrum wall tissue responsive to the output from the sensor while at least a portion of the capsule is being squeezed by the peristaltic contraction of the antrum.

23. A swallowable device for delivering a therapeutic agent preparation into a wall of a patient's stomach, the device comprising:

a capsule sized to pass through the patient's intestinal tract, the capsule having a wall including opposing side portions and opposing end portions, the capsule having an elongated shape configured to longitudinally orient within the antrum of the stomach during a peristaltic contraction of the stomach such that a side portion of the capsule wall is adjacent a wall of the antrum;

a therapeutic preparation in the capsule, the preparation comprising a therapeutic agent and shaped as a tissue penetrating member;

a sensor disposed in one of the opposed side portions of the capsule wall, the sensor configured to sense a force applied by the antrum wall to the capsule and to generate an electrical output upon sensing said force;

logic means configured to analyze the electrical output from the sensor and generate a trigger signal when a peristaltic contraction in the antrum is detected; and ejection means operatively coupled to the tissue penetrating member and the logic means, wherein the ejection means ejects the tissue penetrating member from the capsule into antrum wall tissue responsive to the trigger signal quickly enough such that the tissue penetrating member is ejected from the capsule into the antrum wall tissue while the antrum is in a state of peristaltic contraction.

* * * * *